(12) United States Patent
Takahashi et al.

(10) Patent No.: US 11,517,679 B2
(45) Date of Patent: Dec. 6, 2022

(54) SYRINGE SYSTEM AND USAGE METHOD OF THE SAME

(71) Applicant: TERUMO KABUSHIKI KAISHA, Tokyo (JP)

(72) Inventors: Hiroaki Takahashi, Kanagawa (JP); Hitoshi Okihara, Shizuoka (JP); Yuki Kobarai, Tokyo (JP)

(73) Assignee: TERUMO KABUSHIKT KAISHA, Tokyo (JP)

( * ) Notice: Subject to any disclaimer, the term of this patent is extended or adjusted under 35 U.S.C. 154(b) by 506 days.

(21) Appl. No.: 16/355,547

(22) Filed: Mar. 15, 2019

(65) Prior Publication Data

US 2019/0240418 A1 Aug. 8, 2019

Related U.S. Application Data

(63) Continuation of application No. PCT/JP2017/033196, filed on Sep. 14, 2017.

(30) Foreign Application Priority Data

Sep. 16, 2016 (JP) .............................. JP2016-181563

(51) Int. Cl.
*A61M 5/315* (2006.01)
*A61M 5/24* (2006.01)

(52) U.S. Cl.
CPC ...... *A61M 5/31528* (2013.01); *A61M 5/2422* (2013.01); *A61M 5/315* (2013.01); *A61M 5/31515* (2013.01); *A61M 2005/2414* (2013.01); *A61M 2005/2433* (2013.01); *A61M 2005/2492* (2013.01)

(58) Field of Classification Search
CPC ............ A61M 5/31528; A61M 5/2422; A61M 5/315; A61M 5/31515; A61M 2005/2414; A61M 2005/2433; A61M 2005/2492; A61M 5/31526
See application file for complete search history.

(56) References Cited

U.S. PATENT DOCUMENTS

| | | | | |
|---|---|---|---|---|
| 5,620,423 | A | * | 4/1997 | Eykmann .......... A61M 5/31513 604/218 |
| 2014/0330206 | A1 | * | 11/2014 | Moore .................... A61M 5/20 604/152 |
| 2015/0165135 | A1 | * | 6/2015 | McLoughlin ......... A61M 5/002 604/111 |

FOREIGN PATENT DOCUMENTS

CN 2574697 Y 9/2003
DE 43 32 308 C1 9/1994
(Continued)

OTHER PUBLICATIONS

Extended European Search Report dated Feb. 4, 2020 in corresponding European Patent Application No. 17850956.8.
(Continued)

*Primary Examiner* — James D Ponton
(74) *Attorney, Agent, or Firm* — Foley & Lardner LLP

(57) ABSTRACT

A syringe system includes a syringe and a pressurization device for a syringe. The pressurization device for a syringe is configured so that the plunger advances by a forward rotation of the plunger, and the plunger retracts by a reverse rotation of the plunger. The plunger is advanceable by pressing the gasket at the time of the forward rotation and is retractable with respect to the barrel without pulling the gasket in the proximal end direction at the time of the reverse rotation.

5 Claims, 13 Drawing Sheets

(56) References Cited

FOREIGN PATENT DOCUMENTS

| | | |
|---|---|---|
| EP | 2 502 599 A1 | 9/2012 |
| GB | 2 266 463 A | 11/1993 |
| JP | 2005-535415 A | 11/2005 |
| JP | 2007-530235 A | 11/2007 |
| WO | WO-2013/079643 A1 | 6/2013 |

OTHER PUBLICATIONS

International Searching Authority, "International Search Report," issued in connection with International Patent Application No. PCT/JP2017/033196, dated Dec. 5, 2017.

International Searching Authority, "Written Opinion," issued in connection with International Patent Application No. PCT/JP2017/033196, dated Dec. 5, 2017.

Office Action and Search Report dated Dec. 30, 2020 in corresponding Chinese Patent Application No. 201780056233.5.

* cited by examiner

SYRINGE SYSTEM AND USAGE METHOD OF THE SAME

CROSS-REFERENCE TO RELATED APPLICATIONS

This is a bypass continuation of PCT Application No. PCT/JP2017/033196, filed on Sep. 14, 2017, which claims priority to Japanese Application No. 2016-181563, filed on Sep. 16, 2016. The contents of these applications are hereby incorporated by reference in their entireties.

BACKGROUND

The present disclosure relates to a syringe system including a prefilled syringe and a pressurization device for a syringe, and a method of using the same.

In related art, a so-called threaded syringe configured to advance a plunger by a screwing action of a screw in order to discharge a liquid medicine having a relatively high viscosity from a syringe barrel has been known (for example, see JP 2005-535415 A).

A threaded syringe of JP 2005-535415 A is equipped with a syringe barrel, a grip (a sliding part 14) and a plunger. The grip is attachable to a flange of the syringe barrel and is slidable along the flange of the syringe barrel in an attached state. The grip has a threaded hole and an unthreaded hole. A male screw is disposed on an outer circumferential surface of a shaft of the plunger. The syringe can be used as an unthreaded syringe operated by pushing the plunger when the unthreaded hole of the grip is aligned with the syringe barrel. The syringe can be used as a threaded syringe when the threaded hole of the grip is aligned with the syringe barrel.

SUMMARY

In JP 2005-535415 A, when the syringe is used as the threaded syringe, pressurization in the syringe barrel can be released by shifting the grip to a position at which the unthreaded hole is aligned with the syringe barrel, but it is necessary to shift the grip for releasing the pressurization, and the operation is complicated. Further, there is a possibility that the grip may be unintentionally shifted and the pressurization may be released.

Certain embodiments of the present disclosure have been developed in view of such problems, and one object of certain embodiments is to provide a syringe system capable of releasing pressurization by a simple operation and capable of inhibiting unintentional release of pressurization, and a method of using the same.

A syringe system according to one embodiment includes a prefilled syringe including a barrel, a gasket disposed to be slidable inside the barrel, and a liquid medicine filled in a liquid chamber formed by the barrel and the gasket; and a pressurization device for a syringe attachable to the prefilled syringe. The pressurization device for a syringe includes a plunger configured to press the gasket disposed in the barrel in a distal end direction, and the pressurization device for a syringe is configured so that the plunger advances in the distal end direction by a forward rotation of the plunger, and the plunger retracts in a proximal end direction by a reverse rotation of the plunger. The plunger is configured to advance while pushing the gasket in the distal end direction at the time of the forward rotation, and to retract with respect to the barrel without pulling the gasket in the proximal end direction at a time of the reverse rotation. The gasket is configured to retract in the proximal end direction by a pressure of the liquid medicine increased at a time of the forward rotation of the plunger, without being pulled with the plunger at the time of the reverse rotation of the plunger.

According to the syringe system described above, when the plunger is rotated in the reverse direction from the state in which the liquid medicine in the barrel is discharged, the plunger retracts with respect to the barrel. As a result, the gasket retracts, the pressurization in the barrel is released, and the discharge of the liquid medicine is stopped. Therefore, it is possible to release the pressurization by a simple operation and to inhibit unintentional release of pressurization. In addition, because the gasket is retracted by the pressure in the barrel without pulling the gasket in the proximal end direction with the plunger, it is possible to inhibit the suction of the liquid medicine due to excessive retraction of the plunger.

In the above syringe system, the liquid medicine may have a viscosity in a range of 50 to 120 mPa·s.

Because the liquid medicine has such a viscosity, the pressure of the liquid medicine increased at the time of the forward rotation of the plunger is maintained until immediately before the reverse rotation. Thus, at the time of reverse rotation, the gasket reliably retracts in the proximal end direction by the pressure of the liquid medicine, and the pressurization is released.

According to another embodiment, there is provided a method of using a syringe system equipped with a prefilled syringe including a barrel with a nozzle disposed at a distal end, a gasket disposed to be slidable inside the barrel, and a high-viscosity liquid medicine filled in a liquid chamber formed by the barrel and the gasket; and a pressurization device for a syringe including a plunger configured to press the gasket disposed in the barrel in a distal end direction and configured so that the plunger advances by a forward rotation of the plunger and the plunger retracts by a reverse rotation of the plunger, the method including: pressing the gasket by the forward rotation of the plunger, thereby applying pressure to the liquid medicine in the barrel to discharge the liquid medicine from the barrel; and retracting the plunger without pulling the gasket in a proximal end direction by the reverse rotation of the plunger, and retracting the gasket by the pressure of the liquid medicine in the barrel to stop the discharge of the liquid medicine.

According to the method described above, when the plunger is rotated in the reverse direction from the state in which the liquid medicine in the barrel is discharged, the plunger retracts with respect to the barrel. As a result, the gasket retracts, the pressurization in the barrel is released, and the discharge of the liquid medicine is stopped. Therefore, it is possible to release the pressurization by a simple operation and to inhibit unintentional release of pressurization. In addition, because the gasket is retracted by the pressure of the liquid medicine in the barrel without pulling the gasket in the proximal end direction with the plunger, it is possible to inhibit the suction of the liquid medicine due to excessive retraction of the plunger.

In the above method of using the syringe system, the liquid medicine may have a viscosity in a range of 50 to 120 mPa·s.

According to certain embodiments of the present disclosure, it is possible to release the pressurization by a simple operation of the plunger and to inhibit unintentional release of pressurization.

DETAILED DESCRIPTION

Certain embodiments of the present invention will be described below with reference to the accompanying drawings.

Figure 1:
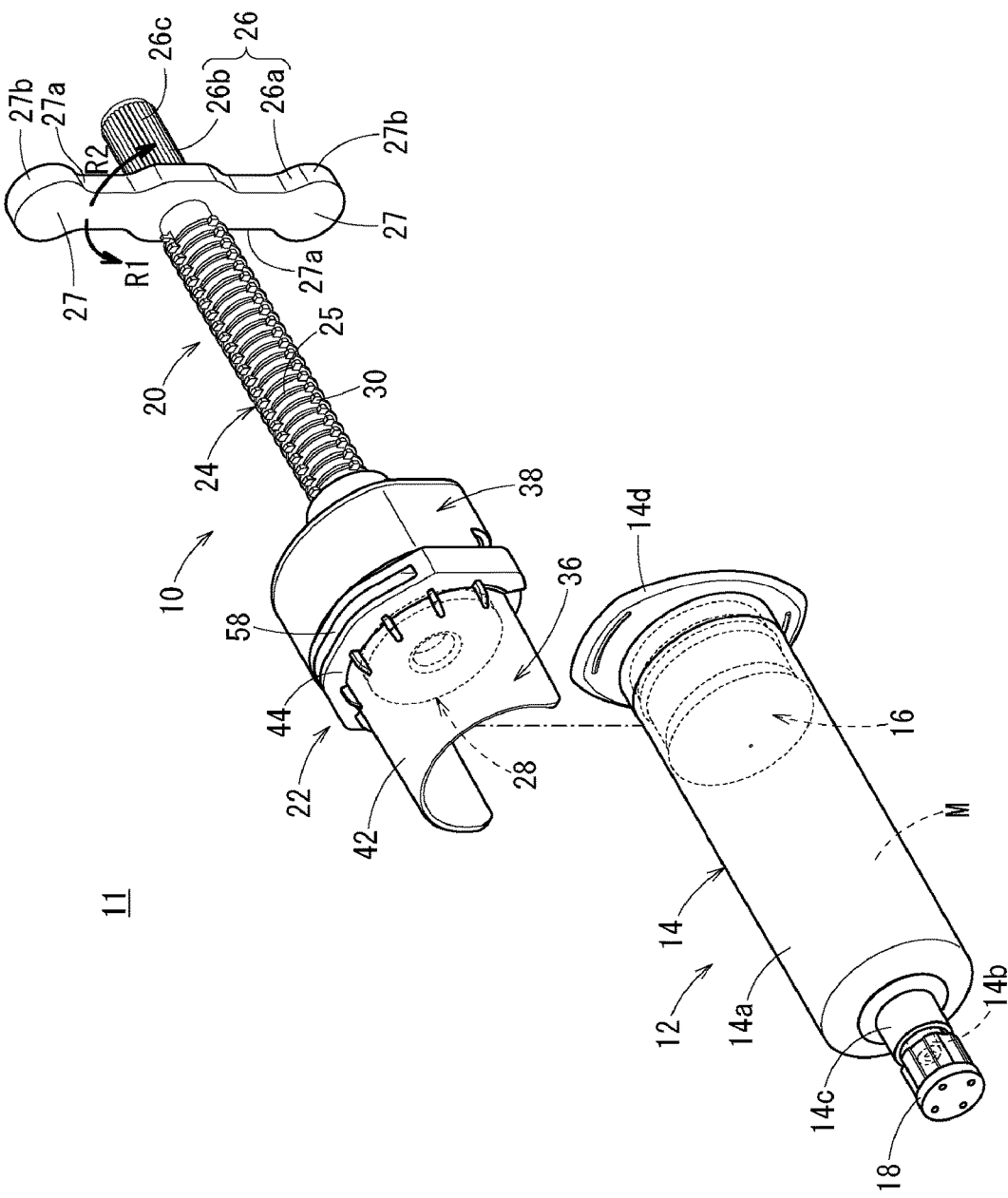
FIG. 1 is a perspective view of a syringe system including a syringe and a pressurization device for a syringe.

A pressurization device 10 for a syringe (hereinafter abbreviated as a "pressurization device 10") illustrated in FIG. 1 is a device that is attached to a syringe 12 and is used for discharging a liquid medicine M in the syringe 12 by pressing a gasket 16 of the syringe 12 in a distal end direction. The syringe system 11 is constituted by the syringe 12 and the pressurization device 10.

In FIG. 1, the syringe 12 includes a hollow tubular barrel 14, a gasket 16 (also referred to as a stopper) disposed inside the barrel 14 to be axially slidable in a liquid-tight manner, and the liquid medicine M filled in a liquid chamber formed by the barrel 14 and the gasket 16. That is, the syringe 12 is configured as a prefilled syringe in which the liquid medicine M is prefilled in the barrel 14.

The liquid medicine M has a relatively high viscosity such that the pressurization device 10 is required for discharging from the syringe 12. For example, a sodium hyaluronate solution can be used. The viscosity of the liquid medicine M is, for example, in a range of 50 to 120 mPa·s.

The barrel 14 includes a barrel body portion 14a having a substantially tubular shape and having a proximal end opening portion formed at a proximal end thereof, a nozzle 14b (see also FIG. 7) disposed at the distal end of the barrel body portion 14a, a lock adapter 14c disposed on the outer side of the nozzle 14b, and a flange 14d protruding radially outward from the proximal end of the barrel body portion 14a.

The barrel 14 is set to have a capacity capable of injecting a relatively large amount of liquid medicine M by a single injection operation. The capacity of the barrel 14 is, for example, in a range of 5 to 100 mL. Therefore, an outer diameter of the barrel body portion 14a is set to a relatively large diameter, for example, in a range of 14 to 36 mm.

The nozzle 14b is reduced in diameter from the center of the distal end of the barrel body portion 14a with respect to the barrel body portion 14a and extends in the distal end direction. The nozzle 14b is configured as a male luer that includes a circular cross-sectional outer shape and includes a tapered outer circumferential surface with an outer diameter reduced in the distal end direction. The nozzle 14b can be fitted to another device having a female luer (for example, a puncturing device 80 to be described below).

In an initial state of the syringe 12 illustrated in FIG. 1, a cap 18 is attached to the nozzle 14b, and the distal end opening portion of the nozzle 14b is sealed in a liquid-tight manner by the cap 18. The cap 18 is detached from the nozzle 14b when the syringe 12 is used. An outer circumferential portion of the gasket 16 comes into contact with an inner circumferential surface of the barrel body portion 14a in a liquid tight manner, and the gasket 16 is disposed to be slidable in the barrel body portion 14a.

The pressurization device 10 includes a syringe plunger 20 (hereinafter, abbreviated as a "plunger 20") capable of pressing the gasket 16 in the distal end direction, and a grip 22 that can be attached to the barrel 14 and supports the plunger 20. The plunger 20 is displaced in an axial direction with respect to the grip 22 with rotation by the screwing action of the screw. The plunger 20 advances with respect to the grip 22 by a forward rotation and retracts with respect to the grip 22 by a reverse rotation.

Figure 2:
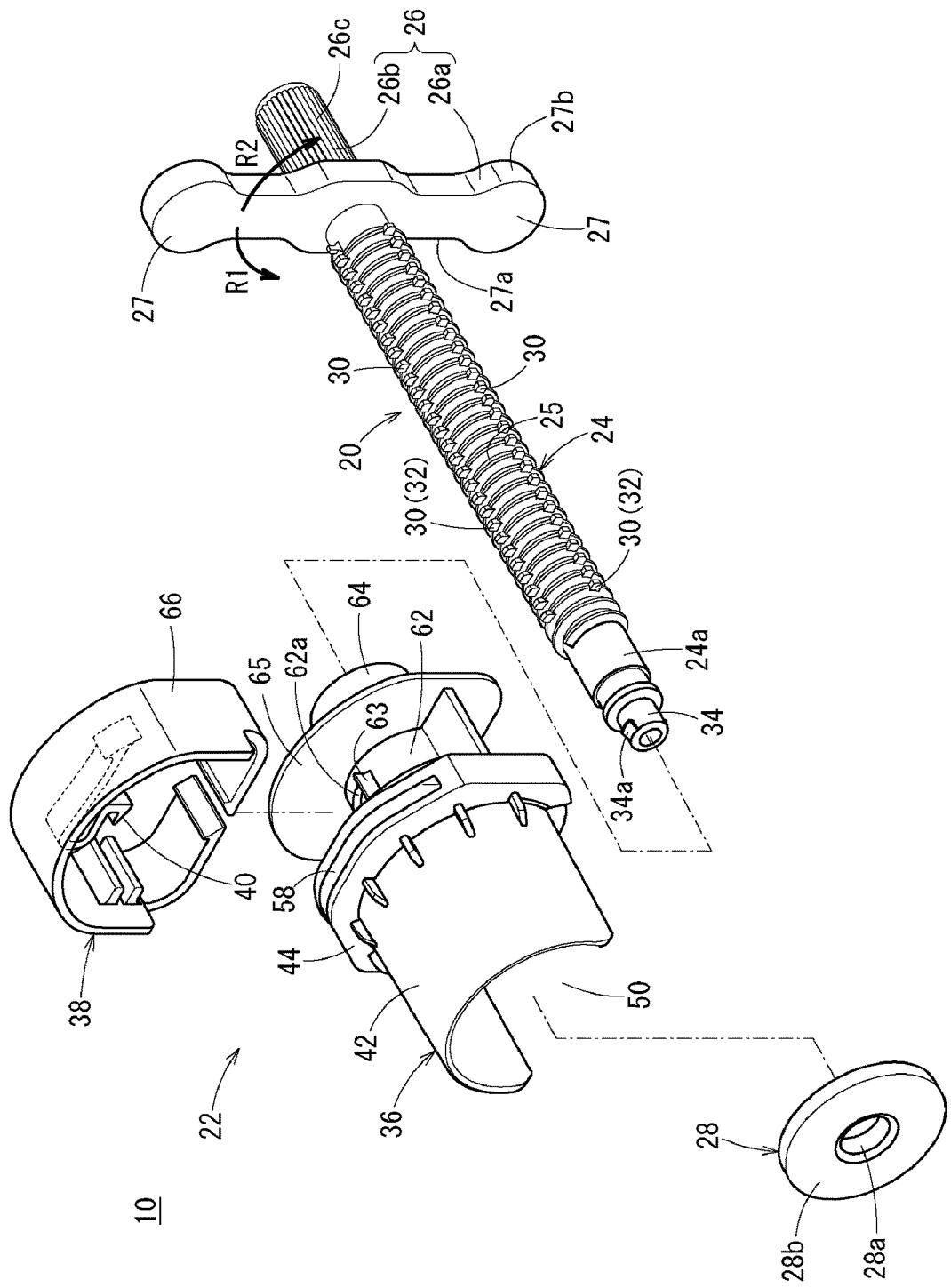
FIG. 2 is an exploded perspective view of the pressurization device for the syringe.

As illustrated in FIG. 2, the plunger 20 includes a plunger rod 24 having a screw thread 25 on its outer circumferential surface, a rotary operation part 26 disposed at the proximal end portion of the plunger rod 24, and a pressing part 28 disposed at the distal end portion of the plunger 20. The plunger rod 24 includes a shaft part 24a that is a rod main body, and the screw thread 25 is formed on the outer circumferential surface of the shaft part 24a. The screw thread 25 extends spirally in a range from the proximal end portion of the shaft part 24a to the vicinity of the distal end portion.

On the top of the screw thread 25, a pressing protrusion 30 protruding outward (radially outward) from the screw thread 25 is disposed. In the plunger 20, a plurality of pressing protrusions 30 are disposed. Specifically, a large number of pressing protrusions 30 are disposed at equal angle intervals (90° intervals in the illustrated example) on the screw thread 25 extending in a spiral shape. In this embodiment, a protrusion row 32 is constituted by the plurality of pressing protrusions 30 arranged on the same straight line parallel to the axis of the plunger rod 24, and a plurality of protrusion rows 32 is disposed at equal intervals in the circumferential direction.

Figure 5:
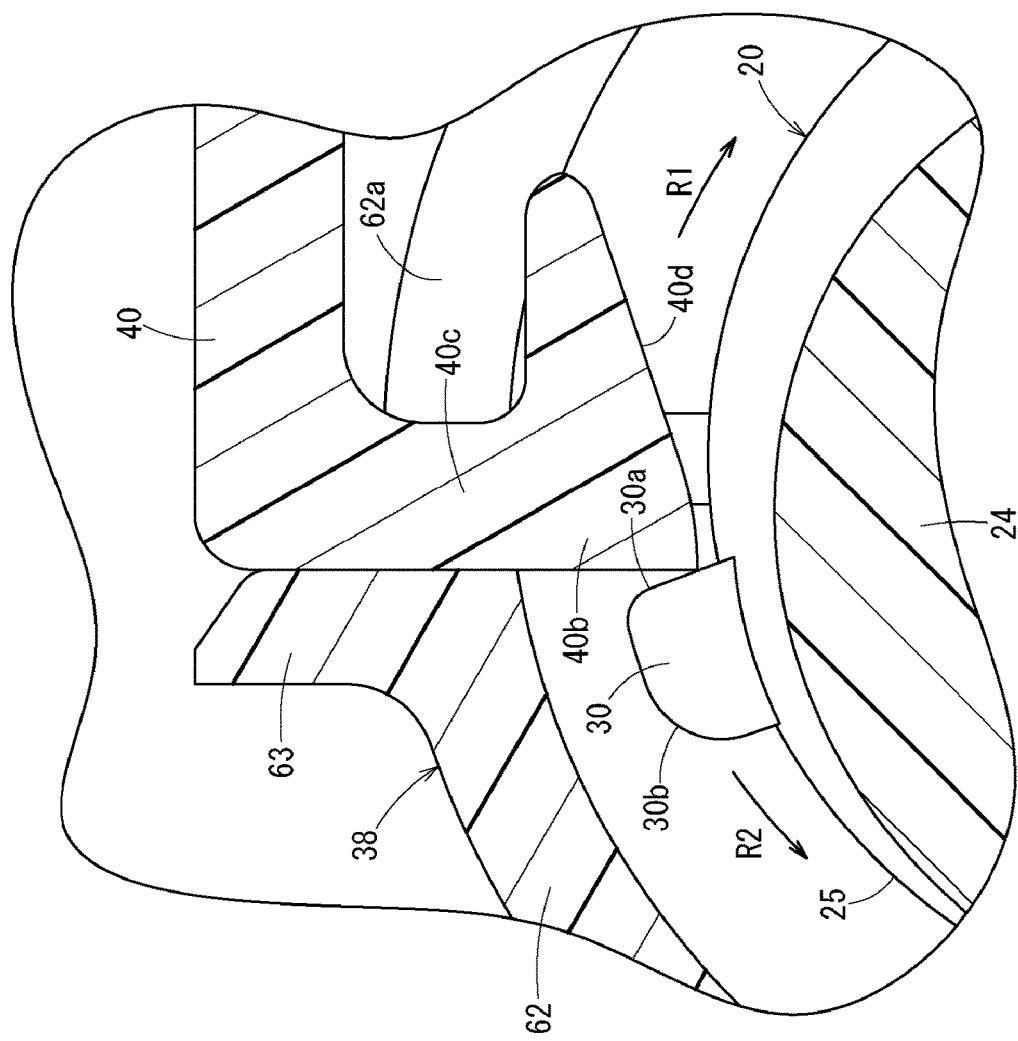
FIG. 5 is a cross-sectional view of a main part of the pressurization device for the syringe.

In FIG. 1, when the plunger 20 is advanced, the plunger 20 is rotated in the forward rotation direction indicated by a direction of an arrow R1, and when the plunger 20 is retracted, the plunger 20 is rotated in the reverse rotation direction indicated by a direction of an arrow R2. As illustrated in FIG. 5, an engaging part 30a substantially perpendicular to the circumferential direction of the plunger 20 is disposed on the side of the pressing protrusion 30 in the forward rotation direction (the direction of the arrow R1). On the other hand, a curved part 30b formed in an arc shape is disposed on the side of the pressing protrusion 30 in the reverse rotation direction (the direction of the arrow R2).

In FIGS. 1 and 2, the rotary operation part 26 is a part that is grabbed by a user's finger for operation in order to rotate the plunger 20. The rotary operation part 26 is disposed so as not to be rotatable with respect to the plunger rod 24. In this embodiment, the rotary operation part 26 is formed integrally with the plunger rod 24.

The rotary operation part 26 includes a finger grip rotary operation part 26a and a knob rotary operation part 26b. The finger grip rotary operation part 26a protrudes in a direction perpendicular to the axis of the plunger rod 24. The finger grip rotary operation part 26a protrudes outward in the radial direction from the plunger rod 24 and the knob rotary operation part 26b.

In the present embodiment, the finger grip rotary operation part 26a includes a pair of rod-like finger grip parts 27 protruding in directions opposite to each other from the plunger rod 24. A constricted part 27a having a relatively small width and a bulging part 27b having a relatively large width disposed outside the constricted part 27a are disposed at the rod-like finger grip part 27. A step difference between the constricted part 27a and the bulging part 27b makes it easier for the user to hook a finger.

The knob rotary operation part 26b protrudes from the finger grip rotary operation part 26a in the proximal end direction coaxially with the plunger rod 24. The knob rotary operation part 26b is formed in a substantially tubular shape. The knob rotary operation part 26b is formed to have an appropriately small diameter so that the plunger 20 can be quickly rotated by the user's fingers in a case in which a large torque is not required when the plunger 20 is rotated. The outer diameter of the knob rotary operation part 26b is, for example, in a range of 3 to 15 mm, preferably in a range of 7 to 10 mm. In the present embodiment, the outer diameter of the knob rotary operation part 26b is smaller than the outer diameter of the screw thread 25.

In order to inhibit the finger from easily sliding when the user pinches the knob rotary operation part 26b with the finger to rotate, a plurality of narrow grooves 26c extending along the axis of the plunger 20 is formed as an anti-slip structure on the outer circumferential surface of the knob rotary operation part 26b at intervals in the circumferential direction. Knurling may be disposed in place of the plurality of narrow grooves 26c.

Figure 3:
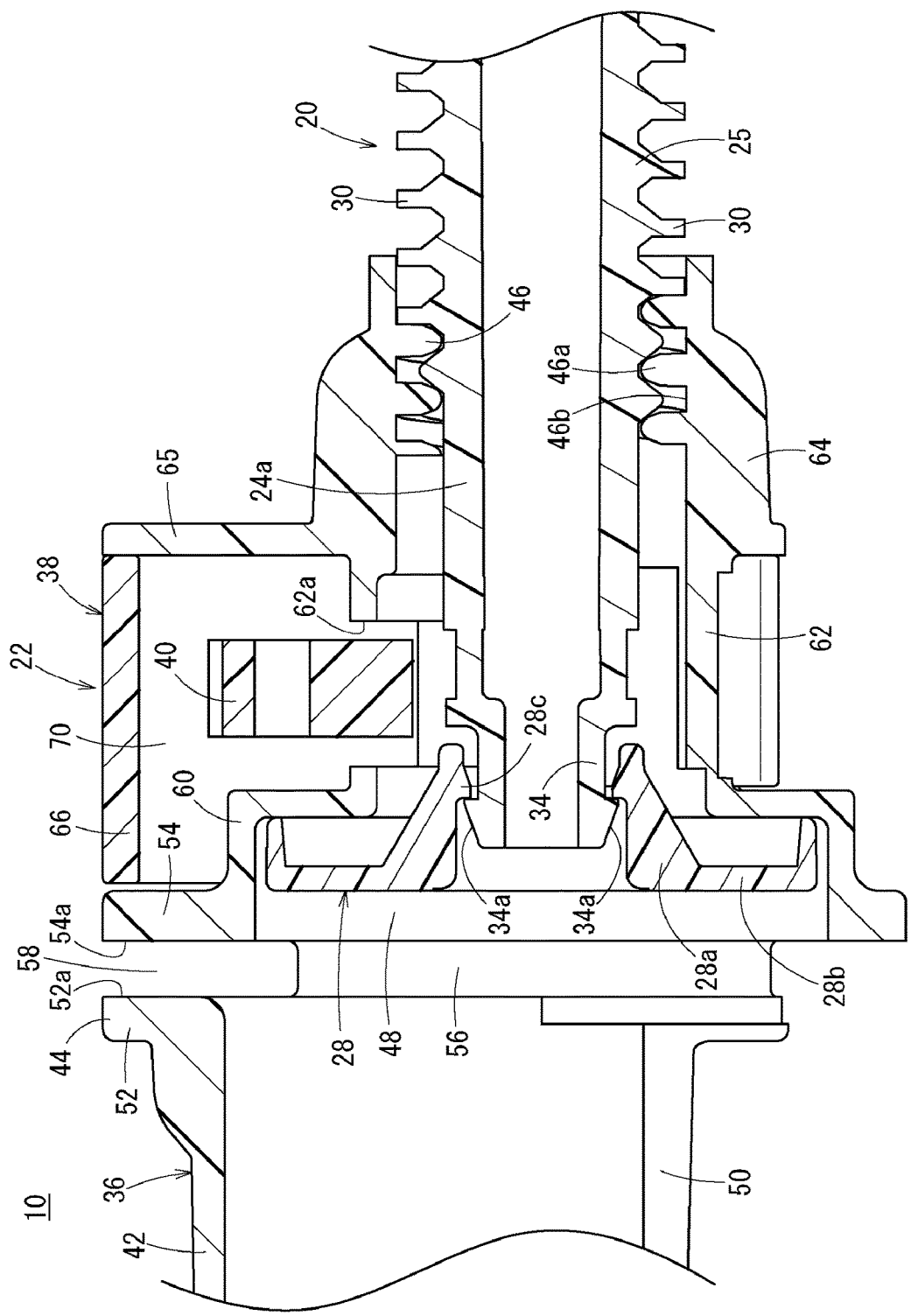
FIG. 3 is a cross-sectional view along an axis of the pressurization device for the syringe.

In FIG. 2, the pressing part 28 is a disk-shaped member that is rotatably supported by the distal end portion of the plunger rod 24 and has a larger diameter than that of the plunger rod 24. As illustrated in FIG. 3, a rotation support part 34 that rotatably supports the pressing part 28 is disposed at the distal end portion of the plunger rod 24 (the shaft part 24a). A locking claw 34a protruding outward is disposed at the distal end of the rotation support part 34.

The pressing part 28 includes a tubular base part 28a constituting a center side, and a ring-shaped abutting part 28b extending outward from the tubular base part 28a. On the inner circumferential surface of the tubular base part 28a, a ring-shaped locking protrusion 28c protruding inward is disposed. The locking claw 34a and the ring-shaped locking protrusion 28c constitute a stopper means for inhibiting the pressing part 28 from being slipped off from the rotation support part 34 in the distal end direction.

Figure 8:
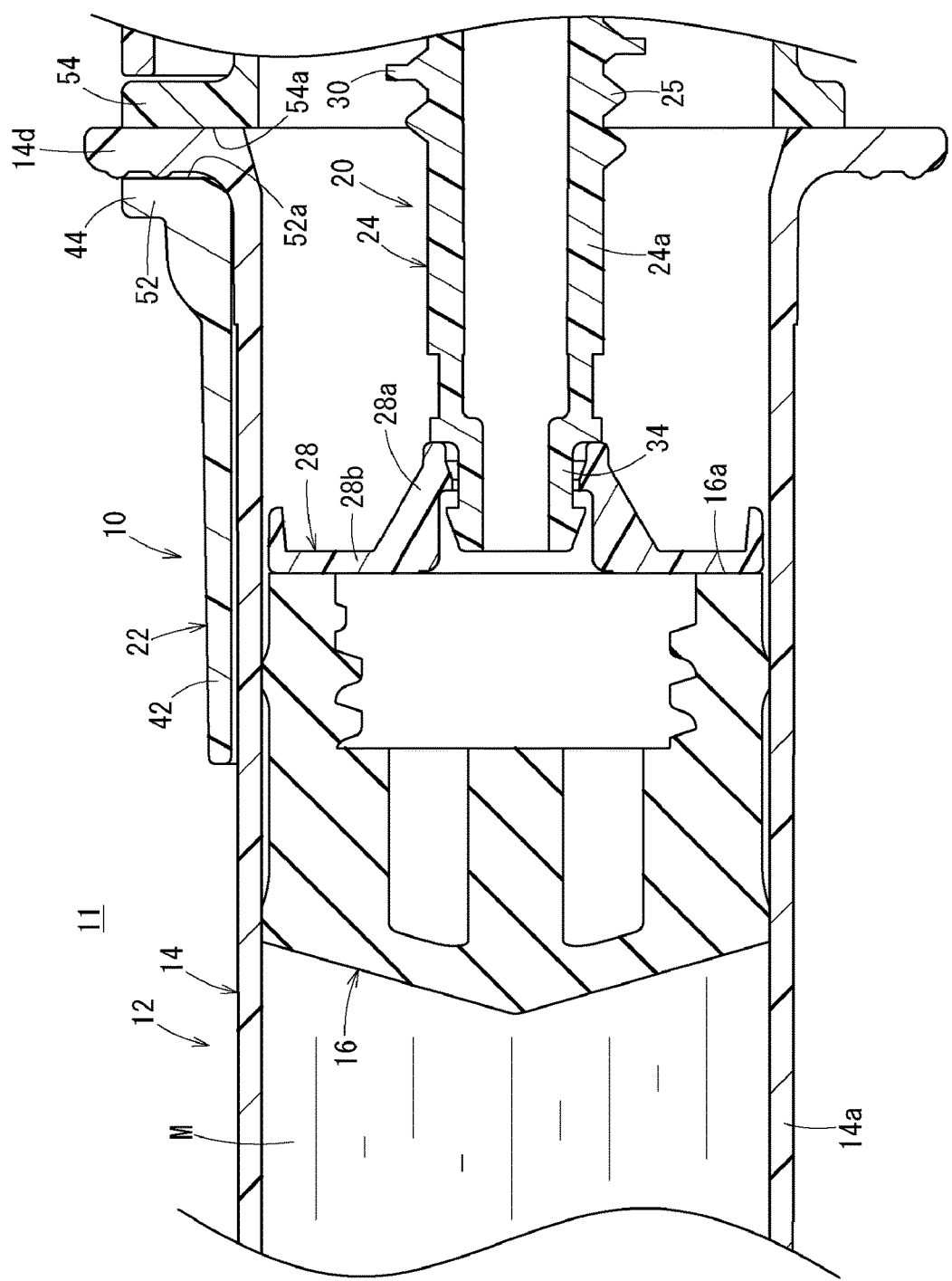
FIG. 8 is a cross-sectional view of a state in which a gasket is advanced by a plunger.

As illustrated in FIG. 8, the abutting part 28b is a portion that abuts on the proximal end surface 16a of the gasket 16 when the gasket 16 is pressed. The distal end surface of the abutting part 28b is flat and extends perpendicular to the axis of the plunger 20. The outer diameter of the abutting part 28b is preferably set to be the same as the outer diameter of the proximal end surface 16a of the gasket 16, or is equal to or smaller than the outer diameter of the proximal end surface 16a of the gasket 16 and is close to the outer diameter. In the present embodiment, the outer diameter of the abutting part 28b is set to be approximately the same as the outer diameter of the proximal end surface 16a of the gasket 16.

In FIG. 1, the grip 22 is configured to be attachable to the barrel 14 from a direction perpendicular to the axis of the barrel 14. As illustrated in FIG. 2, the grip 22 includes a first member 36 constituting a grip main body portion, and a second member 38 fixed to the first member 36 and provided with a displacement mechanism part 40.

As illustrated in FIG. 3, the first member 36 includes a barrel attachment part 42 attachable to the outer circumferential surface of the barrel 14, a flange attachment part 44 attachable to the flange 14d, a female screwing part 46 screwed to the screw thread 25 of the plunger 20, and an accommodation part 48 formed between the flange attachment part 44 and the female screwing part 46.

The barrel attachment part 42 and the flange attachment part 44 are formed with attachment openings 50 (see also FIG. 2) in which the barrel attachment part 42 and the flange attachment part 44 are cut in the axial direction. The barrel attachment part 42 extends in the axial direction by a predetermined length, is curved along the outer circumferential surface of the barrel 14, and is formed in a C-shaped cross section.

The flange attachment part 44 includes a distal end side holding part 52, a proximal end side holding part 54, and a connecting part 56 that connects the distal end side holding part 52 and the proximal end side holding part 54. A holding groove 58 is formed between the distal end side holding part 52 and the proximal end side holding part 54. As illustrated in FIG. 8, in a state in which the grip 22 is attached to the barrel 14, the flange 14d is inserted into the holding groove 58, and the flange 14d is sandwiched and held between the holding surfaces 52a and 54a facing each other. As a result, relative movement of the grip 22 in the axial direction with respect to the barrel 14 is restricted.

Figure 6:
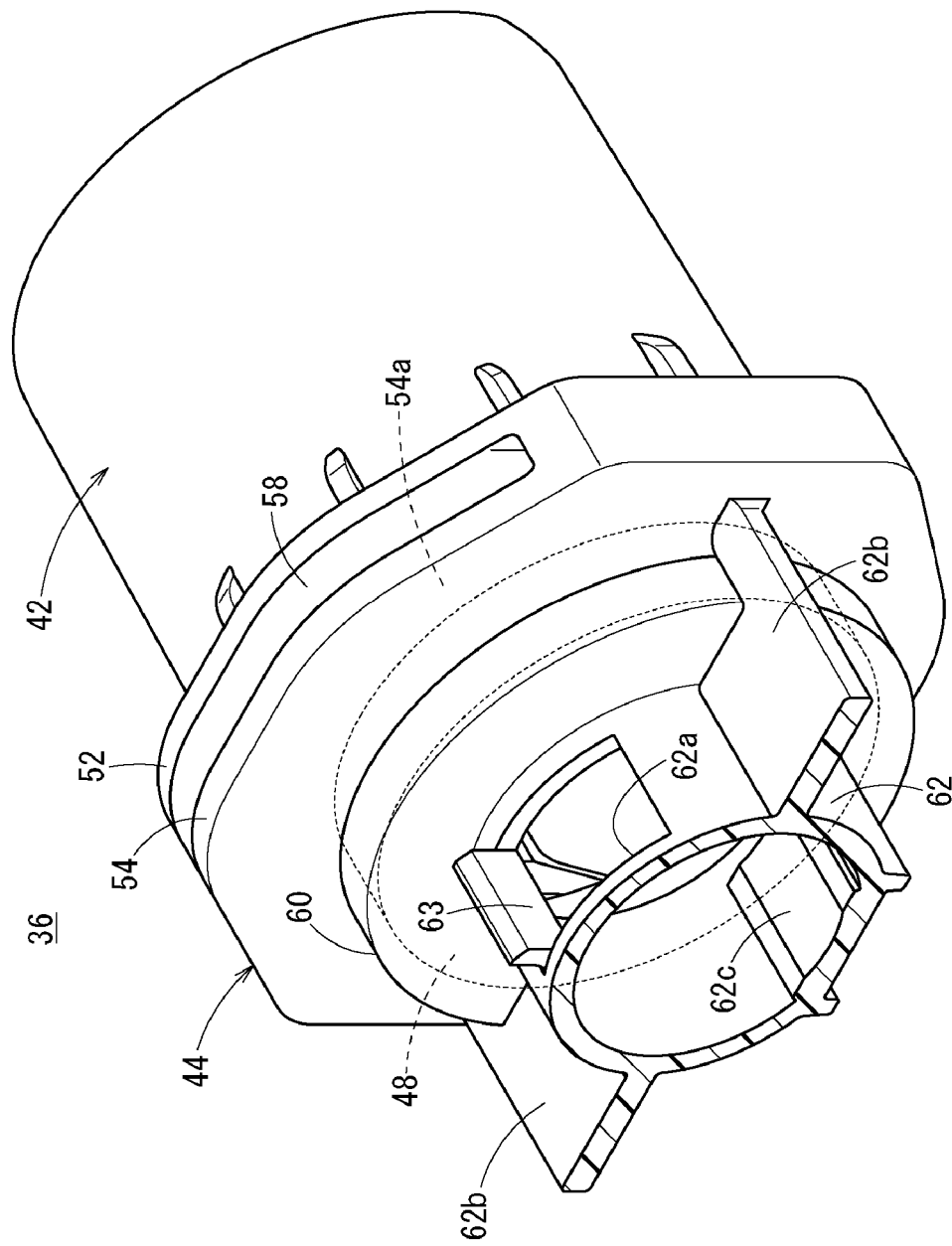
FIG. 6 is a perspective cross-sectional view from a proximal end side of a first member.

As illustrated in FIG. 3, in the first member 36, an accommodation part forming part 60 is disposed to be adjacent to the proximal end side of the flange attachment part 44, a first tubular part 62 (see also FIG. 2) is disposed to be adjacent to the proximal end side of the accommodation part forming part 60, and a second tubular part 64 (see also FIG. 2) is disposed to be adjacent to the proximal end side of the first tubular part 62. The accommodation part 48 capable of accommodating the aforementioned pressing part 28 of the plunger 20 is formed inside the accommodation part forming part 60. As illustrated in FIG. 6, the accommodation part 48 is a circular groove that is recessed in the proximal end direction with respect to the flange attachment part 44 (specifically, the holding surface 54a of the proximal end side holding part 54) and has an inner diameter larger than the outer diameter of the pressing part 28.

Figure 4:
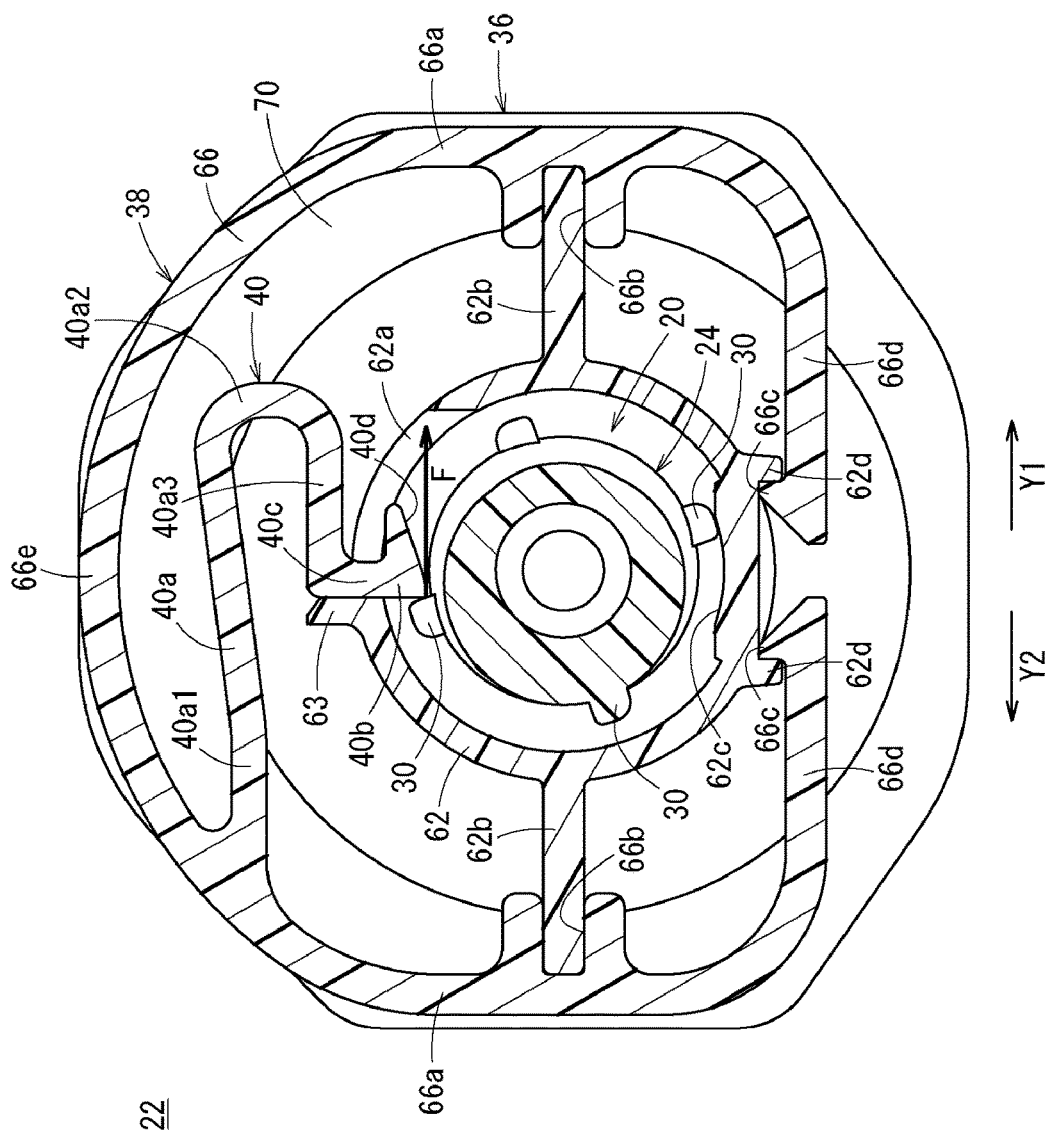
FIG. 4 is a cross-sectional view perpendicular to the axis of the pressurization device for the syringe.

As illustrated in FIGS. 4 and 6, a hole part 62a penetrating a circumferential wall of the first tubular part 62 in the thickness direction is disposed in the first tubular part 62. The displacement mechanism part 40 of the second member 38 is inserted into the hole part 62a. A wall 63 is disposed in the first tubular part 62 to be adjacent to the hole part 62a. The wall 63 protrudes outward from the outer circumferential surface of the first tubular part 62. A pair of fixing ribs 62b protrudes from the outer circumferential surface of the first tubular part 62 in the directions opposite to each other. The wall 63 is disposed at a substantially central position between the pair of fixing ribs 62b in the circumferential direction of the first tubular part 62.

As illustrated in FIG. 4, a rod position restricting part 62c that restricts the position of the plunger rod 24 with respect to the pressed part 40b is disposed on the side opposite to the pressed part 40b on the basis of the plunger rod 24. The rod position restricting part 62c is a portion padded on an arcuate inner circumferential surface of the first tubular part 62. When coming into contact with the pressing protrusion 30, the rod position restricting part 62c restricts the position of the plunger rod 24 so that the pressing protrusion 30 on the opposite side thereof can press the displacement mechanism part 40.

As illustrated in FIG. 3, a female screwing part 46 is formed on the inner circumferential surface of the second tubular part 64. The female screwing part 46 includes a screw thread 46a extending in a spiral shape. A groove 46b between the screw threads 46a adjacent to each other in the axial direction has a depth that permits the pressing protrusion 30 of the plunger 20 to enter. As the female screwing part 46, instead of the screw thread 46a extending in a spiral shape, a protruding part configured to be screwed to the screw thread 25 as the male screwing part of the plunger 20 may be disposed.

As illustrated in FIGS. 2 and 4, the second member 38 includes a fixing base part 66 that is fixed to the first member 36 and supports the displacement mechanism part 40. The displacement mechanism part 40 extends from the inner surface of the fixing base part 66. The fixing base part 66 is formed in a C shape to partially surround the first tubular part 62 of the first member 36.

As illustrated in FIG. 4, a pair of fitting grooves 66b is disposed on the inner surfaces of the mutually facing side walls 66a of the fixing base part 66. A pair of fixing ribs 62b of the first member 36 is fitted to the pair of fitting grooves 66b, respectively. Therefore, the second member 38 is positioned with respect to the first member 36 in a direction perpendicular to the axis of the first member 36.

A pair of engaging claws 66c is disposed at both circumferential end portions of the fixing base part 66. Specifically, the pair of engaging claws 66c is formed at the end portions of a pair of arms 66d that is curved from the side walls 66a on both sides and extends inward. The pair of engaging claws 66c is engaged with an engaging protrusion 62d disposed on the first member 36 (specifically, the first tubular part 62). Thus, the fixing of the second member 38 to the first member 36 becomes more rigid. Further, the engaging claw 66c and the engaging protrusion 62d may not be disposed.

As illustrated in FIG. 3, the second member 38 is held between a proximal end side holding part 54 and a flange-like wall part 65 protruding outward from the outer circumferential surface of the second tubular part 64. As a result, the second member 38 is positioned with respect to the first member 36 in the axial direction of the first member 36. An internal space 70 surrounded by the first member 36 and the second member 38 is formed inside the second member 38, and the displacement mechanism part 40 is disposed in the internal space 70.

As illustrated in FIG. 4, the displacement mechanism part 40 extends from a dome-shaped intermediate wall part 66e that connects the side walls 66a on both sides of the fixing base part 66. The displacement mechanism part 40 is displaced substantially along a direction of a tangential force F acting on the pressing protrusion 30 that starts to press the displacement mechanism part 40 at the time of the forward rotation of the plunger rod 24. In the present embodiment, the displacement mechanism part 40 includes an elastically deformable elastic piece part 40a functioning as a spring part, and a pressed part 40b and an abutting part 40c disposed on the free end side of the elastic piece part 40a.

The elastic piece part 40a includes a U-shaped curved part that opens in the direction substantially opposite to the direction of the tangential force F acting on the pressing protrusion 30 that starts to press the displacement mechanism part 40 at the time of the forward rotation of the plunger rod 24. The elastic piece part 40a extends from the support part (the fixing base part 66) along the direction (a direction of an arrow Y1) in which the pressed part 40b is pressed and displaced at the time of the forward rotation of the plunger 20. The fixed end portion of the elastic piece part 40a is disposed at a position away from the wall 63 in a direction (a direction of an arrow Y2) opposite to the direction in which the pressed part 40b is pressed and displaced at the time of the forward rotation of the plunger 20. The elastic piece part 40a is folded back at a position away from the wall 63 in a direction (the direction of the arrow Y1) in which the pressed part 40b is pressed and displaced at the time of the forward rotation of the plunger 20.

Specifically, the elastic piece part 40a includes a first extending part 40a1 that extends from the support part (the fixing base part 66) along the direction in which the pressed part 40b is pressed and displaced at the time of the forward rotation of the plunger rod 24, a curved extending part 40a2 that extends from an extending distal end of the first extending part 40a1 while being curved in a direction opposite to the extending direction of the first extending part 40a1, and a second extending part 40a3 that extends from the extending distal end of the curved extending part 40a2 in a direction opposite to the extending direction of the first extending part 40a1. The pressed part 40b is disposed at the extending distal end of the second extending part 40a3.

The pressed part 40b is a portion that is pressed by the pressing protrusion 30 when the plunger rod 24 rotates. A tapered part 40d is disposed to be adjacent to the pressed part 40b. The tapered part 40d is inclined so as to be separated from the screw thread 25 in a direction (the direction of the arrow Y1) in which the pressed part 40b is pressed and displaced at the time of the forward rotation of the plunger 20.

The abutting part 28b is a portion that abuts on the wall 63 when the displacement mechanism part 40 repelled by the pressing protrusion 30 collides against the wall 63. In the state illustrated in FIG. 4 in which the pressed part 40b is not pressed by the pressing protrusion 30, the abutting part 28b comes into contact with the wall 63 and the pressed part 40b is positioned inside the first tubular part 62.

The constituent material of the first member 36 is not particularly limited, but examples thereof include resin materials such as polypropylene, polycarbonate, polyamide, polysulfone, polyarylate, ABS, and high-density polyethylene.

The constituent materials of the second member 38 are not particularly limited, but may be selected from the above-mentioned materials described as the constituent material of the first member 36. The constituent material of the second member 38 is preferably a material that is softer and is easily elastically deformed (for example, polyacetal or the like) than the constituent material of the first member 36. By configuring the first member 36 and the second member 38 with different materials, it is possible to have suitable mechanical characteristics for each.

Figure 7:
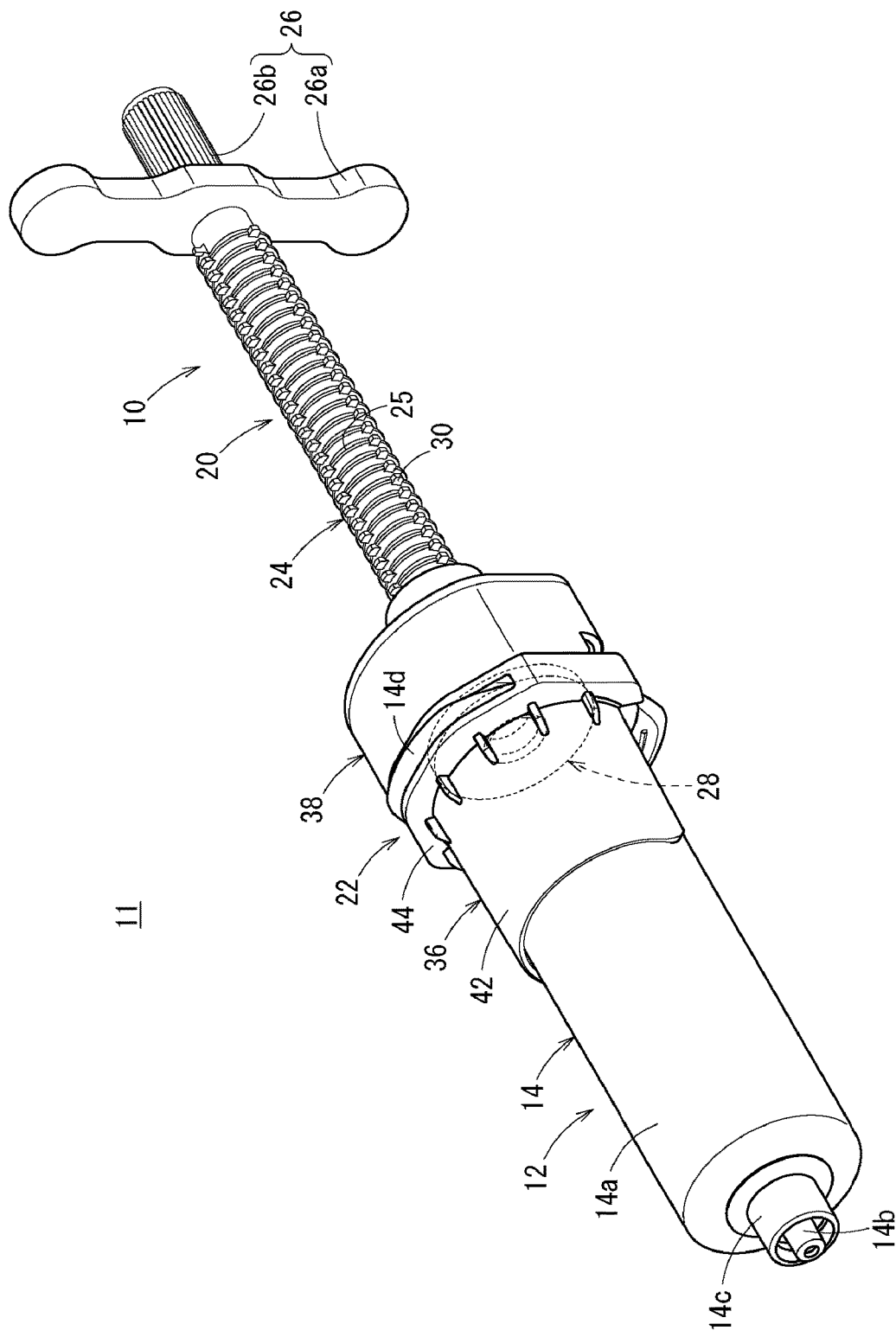
FIG. 7 is a perspective view of an assembled state of the syringe and the pressurization device for the syringe.

Next, the operation of the pressurization device 10 configured as described above will be described. In order to use the syringe 12, the user attaches the pressurization device 10 in which the grip 22 and the plunger 20 are assembled as illustrated in FIG. 7 to the syringe 12. Specifically, the pressurization device 10 is attached to the proximal end portion of the barrel 14 (the proximal end outer circumferential surface of the barrel 14 and the flange 14*d*) from a direction perpendicular to the axis of the barrel 14.

In this case, in the pressurization device 10 according to the present embodiment, the accommodation part 48 (see FIG. 3) capable of accommodating the pressing part 28 of the plunger 20 is disposed between the flange attachment part 44 and the female screwing part 46 of the grip 22. Thus, as illustrated in FIG. 3, the pressing part 28 of the plunger 20 is in a state of being accommodated in the accommodation part 48 of the grip 22 (a state in which the distal end surface of the pressing part 28 is located at the proximal end side of the holding surface 54*a* of the proximal end side holding part 54). As a result, as illustrated in FIG. 7, the pressurization device 10 in which the grip 22 and the plunger 20 are assembled can be attached to the barrel 14 from a direction perpendicular to the axis of the barrel 14 without any trouble. Therefore, one-touch attachment of the pressurization device 10 to the syringe 12 is possible. Further, because the pressurization device 10 is attached to the barrel 14 from the direction perpendicular to the axis of the barrel 14, the pressurization device 10 is not unintentionally detached from the barrel 14 during use.

In this embodiment, in a state in which the pressing part 28 is accommodated at a deepest position with respect to the accommodation part 48, the distal end surface of the pressing part 28 is located at the proximal end side of the most distal end position of the accommodation part 48 (see FIG. 3). Therefore, when the pressurization device 10 is attached to the barrel 14, it is possible to reliably inhibit the pressing part 28 from being caught by the proximal end portion of the barrel 14.

Next, the user detaches the cap 18 (see FIG. 1) from the distal end portion (the nozzle 14*b*) of the syringe 12, connects the distal end portion of the syringe 12 to another device (for example, a puncturing device 80 to be described later), and performs a necessary preparatory work (for example, priming to be described later). Further, as illustrated in FIG. 8, by rotating the plunger 20 in the forward direction, the plunger 20 is advanced and the gasket 16 is pressed in the barrel 14 in the distal end direction. As a result, the gasket 16 advances inside the barrel 14, and the interior of the barrel 14 is pressurized, and thus, the liquid medicine M is discharged from the nozzle 14*b*.

Figure 9A:
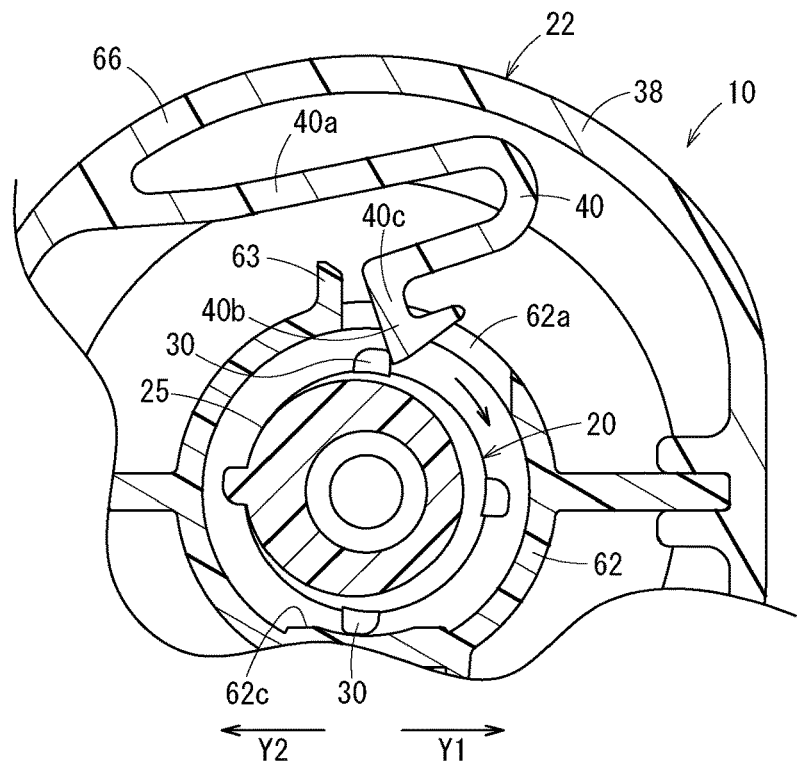
FIG. 9A is an explanatory view of a state in which a pressing protrusion of the plunger that rotates in a forward direction moves a displacement mechanism part of a grip.
Figure 9B:
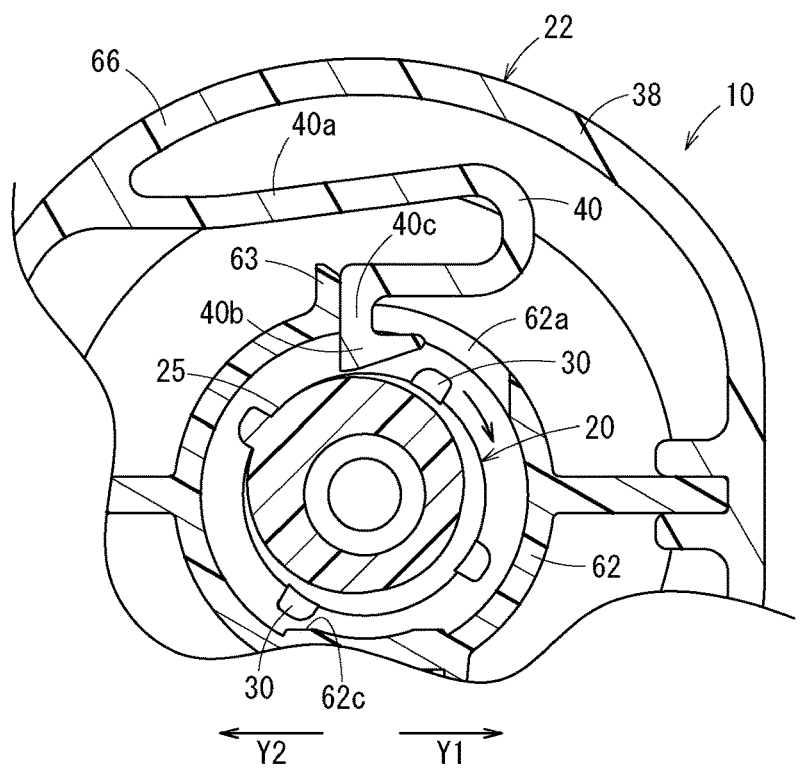
FIG. 9B is an explanatory view of a state in which the displacement mechanism part repelled by the pressing protrusion collides against a wall of the grip.

According to the pressurization device 10 of the present embodiment, when the plunger 20 is rotated in the forward direction for advancement, the pressurization device 10 generates a click sound (and click feeling). That is, when the plunger 20 is rotated for advancement of the gasket 16 inside the syringe 12, as illustrated in FIGS. 9A and 9B, the displacement mechanism part 40 disposed in the grip 22 is repelled by the pressing protrusion 30 disposed on the screw thread 25 of the plunger 20. Further, the displacement mechanism part 40 repelled by the pressing protrusion 30 is displaced by the elastic restoring force and collides against the wall 63 disposed on the grip 22. Therefore, irrespective of the rotational speed of the plunger 20, the magnitude of the generated click sound is constant, and even when the plunger 20 is slowly rotated, the click sound can be reliably generated.

The generation of the click sound will be described in more detail. As illustrated in FIG. 9A, when the plunger 20 rotates in the forward direction, the pressing protrusion 30 disposed on the screw thread 25 presses the pressed part 40*b* of the displacement mechanism part 40, while moving in the circumferential direction. As a result, in the displacement mechanism part 40, the pressed part 40*b* is pressed by the pressing protrusion 30 and displaced in the direction (the direction of the arrow Y1) away from the wall 63 with elastic deformation of the elastic piece part 40*a*. The displacement of the pressed part 40*b* is performed while the engagement (contact) between the pressing protrusion 30 and the pressed part 40*b* is maintained.

Further, when the displacement of the pressing protrusion 30 progresses and the engagement between the pressing protrusion 30 and the pressed part 40*b* is released, as illustrated in FIG. 9B, by the elastic restoring force of the elastic piece part 40*a*, the displacement mechanism part 40 (the abutting part 28*b*) is displaced in the direction (the direction of arrow Y2) opposite to the direction of pressing by the pressing protrusion 30 and collides against the wall 63. The sound generated with the collision is provided to the user as a click sound. The click sound is generated each time the plunger 20 is rotated by a predetermined angle (90° in the present embodiment) in the forward rotation direction.

Therefore, even if the user does not see the scale disposed in the syringe 12, the user can adjust the amount of discharge of the liquid medicine M, using the heard click sound as an indicator. In addition, because the amount of discharge can be grasped by sound (and feeling), the amount of discharge can be adjusted more accurately than the case of adjusting the amount of discharge by observing the scale. For example, the syringe 12 is designed to discharge 1 mL of the liquid medicine M when the plunger 20 makes one revolution, and the pressing protrusion 30 is disposed to generate a click sound once each time the plunger 20 is rotated by 90°. In this case, in order to additionally discharge 0.5 mL from a certain point of time, the user may rotate the plunger 20 so that a click sound is generated twice.

In the present embodiment, the displacement mechanism part 40 is displaced substantially along the direction of the tangential force F (see FIG. 4) acting on the pressing protrusion 30 that starts to press the displacement mechanism part 40 at the time of the forward rotation of the plunger rod 24. With this configuration, because the force received by the pressing protrusion 30 from the displacement mechanism part 40 increases, and the amount of displacement of the displacement mechanism part 40 also increases, a larger click sound can be generated.

In the present embodiment, the displacement mechanism part 40 includes an elastic piece part 40*a* extending from the support part (the fixing base part 66). Therefore, elastic energy can be accumulated with a simple configuration when pressed by the pressing protrusion 30. Moreover, because the elastic piece part 40*a* includes a U-shaped curved part, it is easy to balance well the easiness of deformation of the displacement mechanism part 40 and the strength of the elastic restoring force. Thus, it is possible to generate a clear click sound, while suppressing the increase in the rotation resistance of the plunger 20.

In the present embodiment, a rod position restricting part 62c that restricts the position of the plunger rod 24 with respect to the pressed part 40b is disposed on the side opposite to the pressed part 40b on the basis of the plunger rod 24. Therefore, when the plunger rod 24 rotates, it is possible to reliably press the pressed part 40b in the circumferential direction by the pressing protrusion 30.

Figure 10:
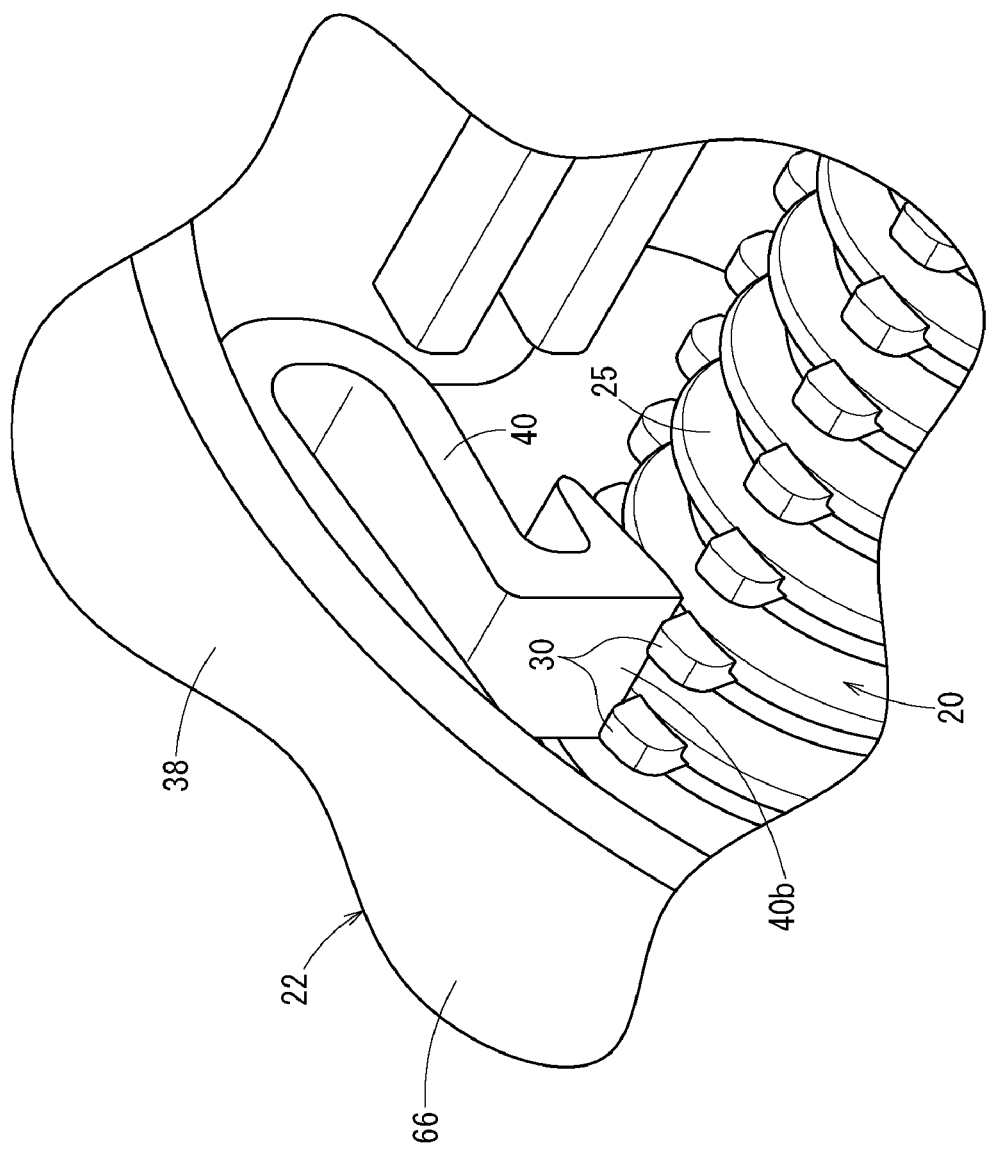
FIG. 10 is an explanatory view of a state in which the two pressing protrusions of the plunger abut on the displacement mechanism part of the grip.

In the present embodiment, as illustrated in FIG. 10, when the plunger 20 rotates in the forward direction, the plurality of pressing protrusions 30 press the displacement mechanism part 40. Therefore, at the time of forward rotation of the plunger 20, the pressing protrusions 30 can be made to reliably abut on the displacement mechanism part 40. In addition, when the pressed part 40b is pressed, the load applied to each pressing protrusion 30 decreases, and breakage of the pressing protrusion 30 can be inhibited.

In the present embodiment, the grip 22 includes an internal space 70 (see FIG. 4) in which the displacement mechanism part 40 is disposed to echo the sound generated with collision of the displacement mechanism part 40 against the wall 63. Therefore, it is possible to amplify a sound pressure level of the click sound generated by the collision of the displacement mechanism part 40 against the wall 63 in the internal space 70, and to provide the user with a clear click sound.

In the present embodiment, the plunger 20 and the pressing part 28 are rotatable relative to each other, and the frictional resistance between the gasket 16 and the pressing part 28 is larger than the frictional resistance between the pressing part 28 and the plunger rod 24. Therefore, as illustrated in FIG. 8, when the gasket 16 is pressed with the rotation of the plunger 20, the gasket 16 advances without rotating inside the barrel 14. Therefore, deformation of the gasket 16 can be suppressed, and the liquid-tightness between the inner surface of the barrel 14 and the gasket 16 can be favorably secured.

In the present embodiment, by rotating the plunger 20 in the reverse direction at the point of time when a predetermined amount of the liquid medicine M is discharged, the pressure inside the barrel 14 can be immediately released, and the discharge of the liquid medicine M can be quickly stopped. That is, when the plunger 20 is rotated in the reverse direction from the state in which the plunger 20 is rotated in the forward direction to discharge the liquid medicine M in the barrel 14, the plunger 20 retracts with respect to the barrel 14. At this time, because the gasket 16 retracts by the pressure of the liquid medicine M increased at the time of the forward rotation of the plunger 20, the pressurization in the barrel 14 is released and the discharge of the liquid medicine M is stopped. Therefore, it is possible to release the pressurization by a simple operation and to inhibit unintentional release of pressurization. In addition, because the gasket 16 is retracted by the pressure inside the barrel 14 without pulling the gasket 16 in the proximal end direction with the plunger 20, it is possible to inhibit suction of the liquid medicine M due to excessive retraction of the plunger 20.

The liquid medicine M has a viscosity in a range of 50 to 120 mPa·s. Because the liquid medicine M has such a viscosity, the pressure of the liquid medicine M increased at the time of the forward rotation of the plunger 20 is maintained until immediately before the reverse rotation. Therefore, at the time of reverse rotation, the gasket 16 is reliably retracted in the proximal end direction by the pressure of the liquid medicine M, and the pressurization is released.

Figure 11A:
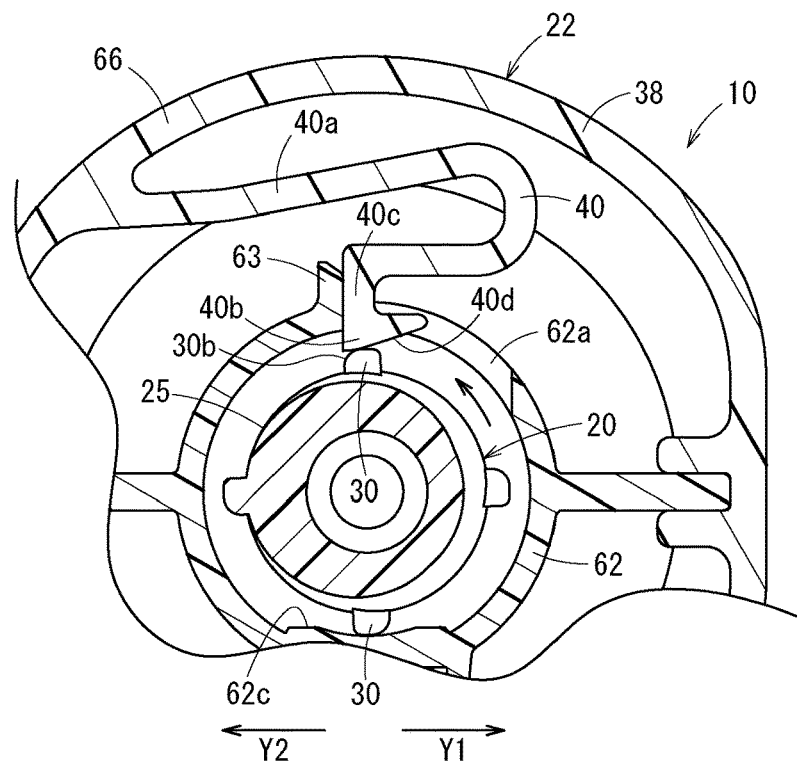
FIG. 11A is an explanatory view of a state in which the displacement mechanism part gets on the pressing protrusion of the plunger that rotates in a reverse direction.
Figure 11B:
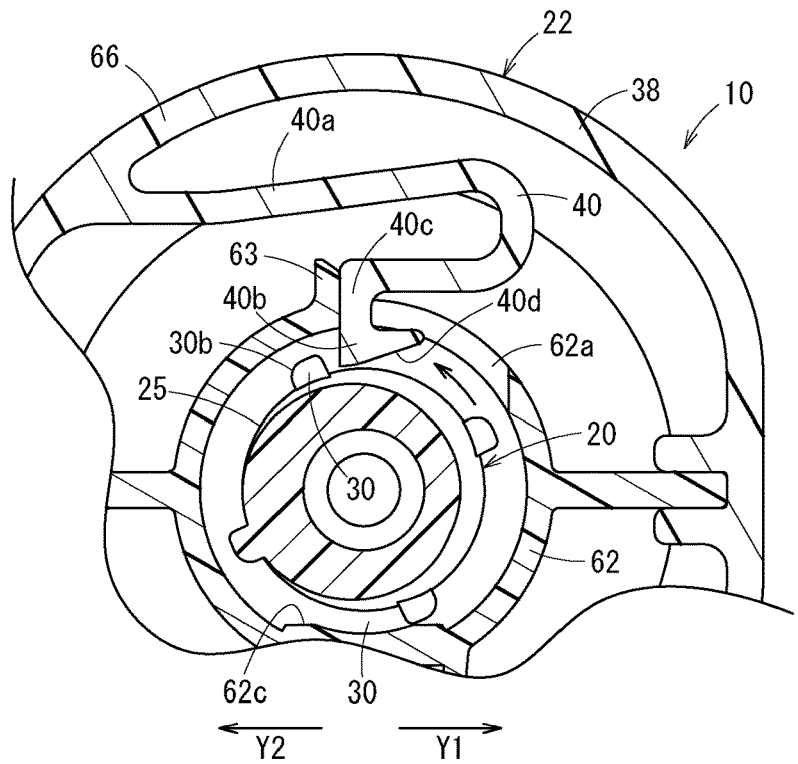
FIG. 11B is an explanatory view of a state in which the displacement mechanism part is disengaged from the pressing protrusion of the plunger that rotates in the reverse direction.

In the present embodiment, when the plunger 20 is rotated in the reverse direction, as illustrated in FIGS. 11A and 11B, the displacement mechanism part 40 is displaced radially outward of the plunger 20 and gets on the pressing protrusion 30. That is, because the reverse rotation of the plunger 20 is not inhibited by the pressing protrusion 30 (the plunger 20 idles in relation to the pressing protrusion 30), the plunger 20 is rotated in the reverse direction to release the pressure inside the syringe 12, and the discharge of the liquid medicine M can be stopped. Further, when the plunger 20 rotates in the reverse direction, because the displacement mechanism part 40 does not collide against the wall 63, the plunger 20 can idle without generating a clear sound like a click sound.

In this case, as illustrated in FIG. 11A, first, the displacement mechanism part 40 contacts the pressing protrusion 30, while being elastically deformed. Because the curved part 30b is disposed at the pressing protrusion 30 and the tapered part 40d is disposed at the displacement mechanism part 40, the pressing protrusion 30 smoothly contacts the pressing protrusion 30. Further, as illustrated in FIG. 11B, when the pressing protrusion 30 is further displaced in the circumferential direction with the reverse rotation of the plunger 20, the displacement mechanism part 40 falls (comes off) from the pressing protrusion 30, and returns to the original shape (is displaced to the plunger 20 side) by the elastic restoring force. At this time, even if the displacement mechanism part 40 comes into contact with the screw thread 25, the impact caused by the contact is considerably smaller than the impact at the time when the abutting part 28b collides against the wall 63 at the time of the forward rotation of the plunger 20.

In the present embodiment, the elastic piece part 40a extends from the support part (the fixing base part 66) along the direction in which the pressed part 40b is pressed and displaced at the time of the forward rotation of the plunger rod 24. Therefore, when the plunger 20 rotates in the reverse direction, the displacement mechanism part 40 is easily deformed radially outward of the plunger 20 along the wall 63. Therefore, the plunger 20 can be rotated in the reverse direction without applying a large torque.

In the present embodiment, as illustrated in FIG. 1, the rotary operation part 26 includes a finger grip rotary operation part 26a protruding in a direction perpendicular to the axis of the plunger rod 24, and a knob rotary operation part 26b protruding in the proximal end direction from the finger grip rotary operation part 26a coaxially with the plunger rod 24. The screw thread 25 can be screwed with a female screwing part 46 disposed in the syringe 12 or attached to the syringe 12, and the plunger 20 can be advanced in the distal end direction by the screwing action between the screw thread 25 and the female screwing part 46 to press the gasket 16 in the distal end direction. Further, the outer diameter of the knob rotary operation part 26b is smaller than the outer diameter of the finger grip rotary operation part 26a. Therefore, when it is not necessary to apply a large torque to the plunger 20, by operating the knob rotary operation part 26b, the plunger 20 can be rotated quickly and the plunger 20 can be advanced quickly. Therefore, the treatment using the syringe 12 can be efficiently performed. That is, depending on the situation, it is possible to select to apply a large torque to the syringe plunger by operating the finger grip rotary operation part 26*a* and to quickly rotate and advance the syringe plunger by operating the knob rotary operation part 26*b*.

In the present embodiment, the finger grip rotary operation part 26*a* protrudes from the screw thread 25 in a direction perpendicular to the axis of the plunger rod 24. Therefore, a larger torque can be applied to the plunger 20.

In particular, in the present embodiment, the outer diameter of the knob rotary operation part 26*b* is smaller than the outer diameter of the screw thread 25. Further, the knob rotary operation part 26*b* has a cylindrical shape. Therefore, when the knob rotary operation part 26*b* is operated by being pinched, the plunger 20 can be easily and more quickly rotated. In addition, because an anti-slip structure for the finger is disposed at the outer circumferential portion of the knob rotary operation part 26*b*, when the knob rotary operation part 26*b* is operated by being pinched, slippage of the finger is suppressed and the operation is easily performed.

Further, the finger grip rotary operation part 26*a* includes a pair of rod-like finger grip parts 27 protruding in opposite directions to each other from the plunger rod 24. For this reason, it is easy to apply a large torque to the plunger 20 when operating the finger grip rotary operation part 26*a* by hooking a finger. In particular, because a constricted part 27*a* and a bulging part 27*b* disposed outside the constricted part 27*a* are disposed in the pair of rod-like finger grip parts 27, when operating the finger grip rotary operation part 26*a* by hooking a finger, the user can easily hook his/her finger.

Next, as an example of a treatment method using the syringe 12 and the pressurization device 10, a case in which an endoscopic submucosal dissection (ESD) or an endoscopic mucosal resection (EMR) is performed will be described. First, the endoscopic submucosal dissection will be described.

The user (surgeon or assistant) attaches the pressurization device 10 to the syringe 12 (pre-filled syringe) filled with the sodium hyaluronate solution M1 and detaches the cap 18 from the syringe 12.

Figure 12:
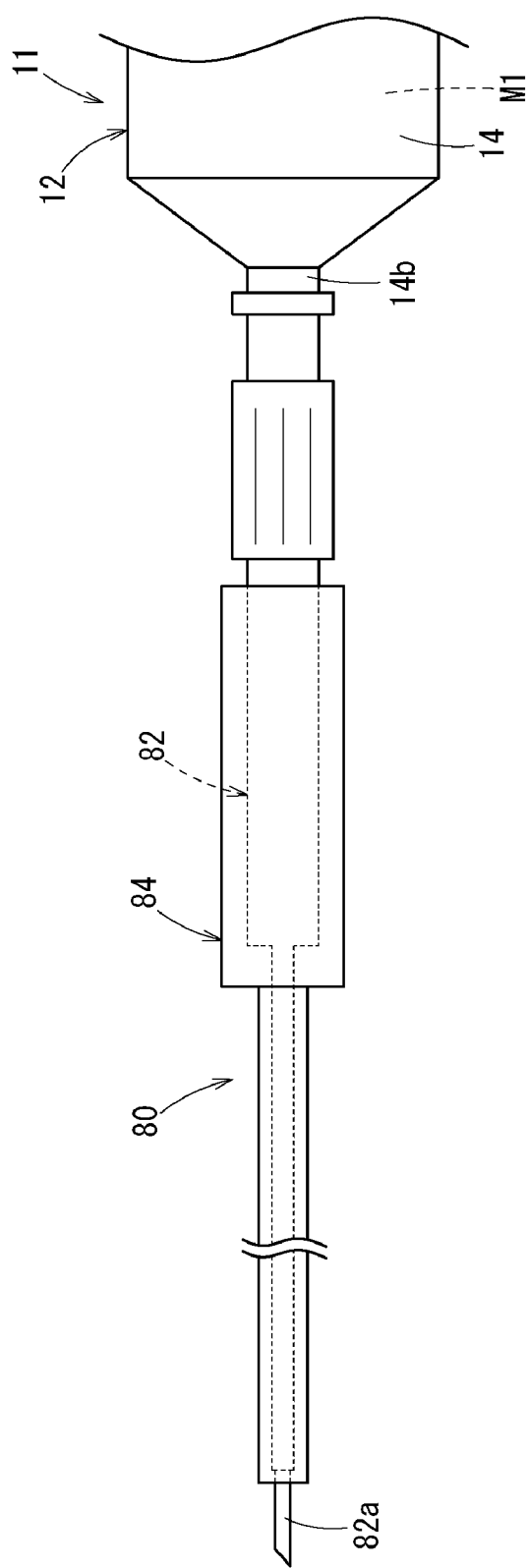
FIG. 12 is an explanatory view of a state in which the syringe is connected to a proximal end portion of a puncturing device and a needle disposed at a distal end portion of an inner catheter of the puncturing device is caused to protrude from the distal end of an outer catheter.

Next, as illustrated in FIG. 12, the user connects the distal end portion (the nozzle 14*b*) of the syringe 12 to the proximal end portion of the inner catheter 82 of the puncturing device 80, and in the state of causing the needle 82*a* to protrude from the outer catheter 84, the plunger 20 is advanced by being rotated, and priming (filling the lumen of the inner catheter 82 and the needle 82*a* with the sodium hyaluronate solution M1) is performed. In this case, until the sodium hyaluronate solution M1 reaches the needle 82*a*, because the rotary operation of the plunger 20 requires only a comparatively small operation force, the user may rotate the plunger 20 by picking the knob rotary operation part 26*b* illustrated in FIG. 1 or the like with a finger. As a result, the plunger 20 can be quickly rotated and the plunger 20 can be advanced quickly.

Further, as illustrated in FIG. 12, the puncturing device 80 includes an inner catheter 82 and an outer catheter 84. The inner catheter 82 is axially slidable with respect to the outer catheter 84 within a restricted range. The needle 82*a* is connected to the distal end of the inner catheter 82. When the inner catheter 82 is located at the retracted position with respect to the outer catheter 84, the needle 82*a* is accommodated within the outer catheter 84. When the inner catheter 82 is located at the advanced position with respect to the outer catheter 84, the needle 82*a* protrudes from the distal end of the outer catheter 84.

Next, the user retracts the inner catheter 82 to accommodate the needle 82*a* in the outer catheter 84. Further, the user inserts the puncturing device 80 into the insertion hole 86*a* (see FIG. 13A) of the endoscope 86.

Figure 13A:
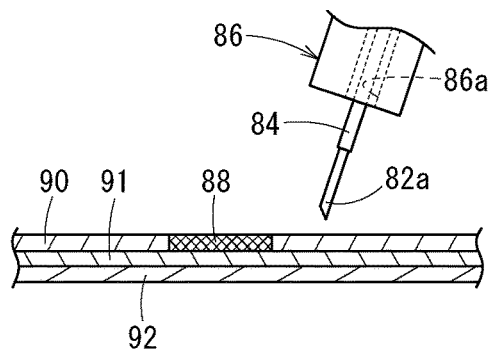
FIG. 13A is an explanatory view of a process of causing the needle of the puncturing device to protrude from a distal end of an endoscope in a living body.

Next, the user, who is a surgeon, causes the needle 82*a* to protrude from the distal end of the endoscope 86 in the digestive tract of the patient as illustrated in FIG. 13A. Further, the user approaches the mucous membrane 90 around the lesioned part 88, and advances the needle 82*a* toward the mucous membrane 90. As a result, the needle 82*a* penetrates the mucous membrane 90 and is punctured into a submucosal layer 91.

Figure 13B:
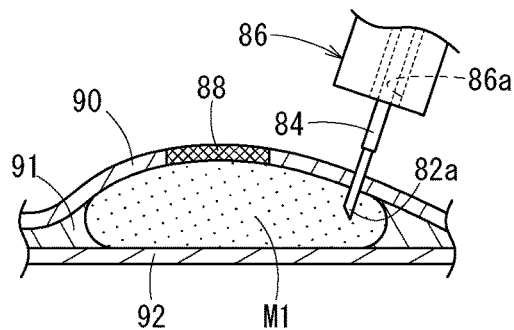
FIG. 13B is an explanatory view of a process of injecting hyaluronic acid into a tissue under the lesioned part to raise the lesioned part.

In this state, as illustrated in FIG. 13B, a predetermined amount of sodium hyaluronate solution M1 is injected into the submucosal layer 91 to raise the lesioned part 88. Specifically, when the hyaluronate solution M1 in the syringe 12 is pressurized by the pressurization device 10 (the plunger 20 is rotated in the forward direction to advance the gasket 16), the sodium hyaluronate solution M1 is injected into the submucosal layer 91 from the distal end opening of the needle 82*a*. The lesioned part 88 is lifted by injection of sodium hyaluronate solution M1. That is, the submucosal layer 91 under the lesioned part 88 is peeled off from the muscular layer 92 and the lesioned part 88 is raised.

In this case, the syringe 12 has a moderate length (a length not too long) that is easy to handle, and the syringe 12 is filled with the sodium hyaluronate solution M1 in an amount sufficient to raise the lesioned part 88 by a single injection. Therefore, the inner diameter of the barrel 14 also has a size corresponding to such an amount. Therefore, in order to inject the sodium hyaluronate solution M1 having a relatively high viscosity via the needle 82*a*, it is necessary to press the gasket 16 in the distal end direction with a large force. In the present embodiment, because the pressurization device 10 is used, it is possible to advance the gasket 16 and inject the sodium hyaluronate solution M1 via the needle 82*a* without requiring an excessive operating force in the operation of the plunger 20.

At the point of time when a predetermined amount of sodium hyaluronate solution M1 is injected, the user rotates the plunger 20 in the reverse direction to release the pressurization. As a result, the discharge of the sodium hyaluronate solution M1 from the syringe 12 stops immediately, and the injection amount of the sodium hyaluronate solution M1 into the submucosal layer 91 can be accurately controlled.

Figure 13C:
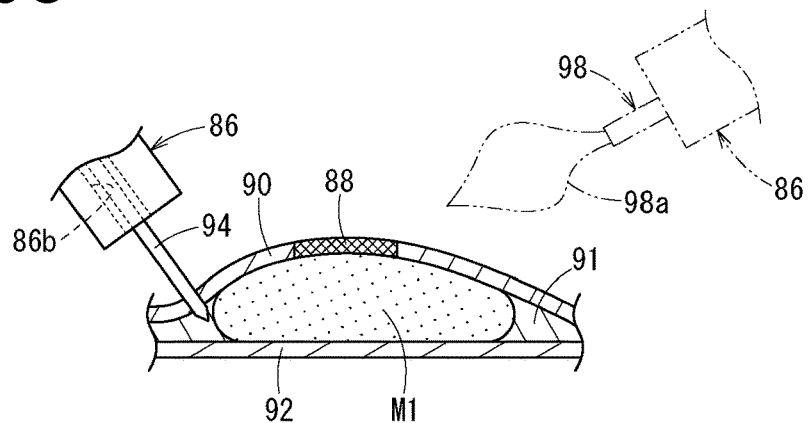
FIG. 13C is an explanatory view of a process of cutting a mucous membrane around the lesioned part by a peeling device.
Figure 13D:
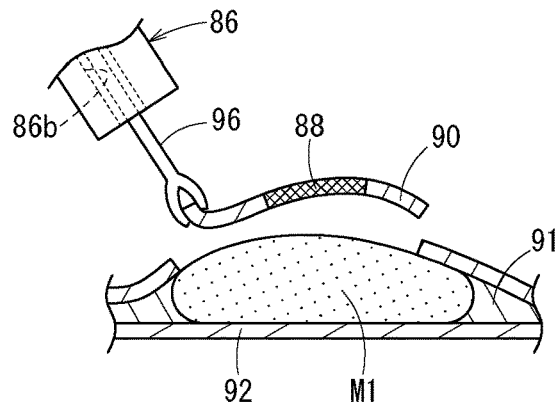
FIG. 13D is an explanatory view of a process of collecting the mucous membrane having the lesioned part by a gripping device.

Next, as illustrated in FIG. 13C, the user inserts a peeling device 94 (an acicular scalpel or the like) into a forceps hole 86*b* of the endoscope 86, and cuts the mucous membrane 90 to surround the lesioned part 88, using the peeling device 94. Next, as illustrated in FIG. 13D, the user inserts a gripping device 96 into the forceps hole 86*b* of the endoscope 86, peels off the mucous membrane 90 having the lesioned part 88, using the gripping device 96, and extracts the peeled mucous membrane 90 to the outside of the body.

On the other hand, when the endoscopic mucosal resection is performed, an ablation device 98 indicated by an imaginary line in FIG. 13C is used instead of the peeling of the mucous membrane 90 by the peeling device 94 described above. The ablation device 98 includes a snare ring 98*a* (a loop-shaped electric scalpel). The user causes the snare ring 98*a* to protrude from the endoscope 86 in the patient's body and hooks the snare ring 98*a* to the mucous membrane 90 around the raised lesioned part 88. Further, when the snare ring 98*a* is squeezed and a high-frequency current flows through the snare ring 98*a*, the mucous membrane 90 having the lesioned part 88 is cut. The cut mucous membrane 90 is collected by the gripping device 96 illustrated in FIG. 13D.

Other procedure processes are performed in the same manner as the above-described endoscopic submucosal dissection.

The present invention is not limited to the above-described embodiments, and various modifications can be made within the scope that does not depart from the gist of the present invention.

What is claimed is:

1. A syringe system comprising:
   a prefilled syringe comprising:
   a barrel,
   a gasket disposed to be slidable inside the barrel, and
   a liquid medicine filled in a liquid chamber formed by the barrel and the gasket; and
   a pressurization device that is attachable to the prefilled syringe, the pressurization device comprising:
   a plunger configured to press the gasket in a distal end direction, wherein the plunger comprises:
   a plunger rod comprising a screw thread at an outer surface of the plunger rod,
   a rotary operation part located at a proximal end portion of the plunger rod,
   a pressing part located at a distal end portion of the plunger rod, and
   a plurality of pressing protrusions that protrude outwardly from the screw thread;
   a grip that is attachable to the barrel of the pre-filled syringe and supports the plunger, the grip comprising:
   a barrel attachment part that is attachable to the barrel of the pre-filled syringe,
   a female screwing part that is screwed to the screw thread of the plunger, and
   a displacement mechanism part configured to be displaced by the pressing protrusions,
   wherein each of the plurality of pressing protrusions comprises an engaging part extending substantially perpendicular to a circumferential direction of the plunger on a side of the pressing protrusion corresponding to a forward rotation direction of the plunger, and a curved part formed in an arc shape on a side of the pressing protrusion corresponding to a reverse rotation direction of the plunger.

2. The syringe system according to claim 1,
   wherein the pressurization device is configured such that the plunger advances in the distal end direction by forward rotation of the plunger, and thereby pushes the gasket in the distal end direction,
   wherein the pressurization device is configured such that the plunger retracts in a proximal end direction by reverse rotation of the plunger, without pulling the gasket in the proximal end direction, and
   wherein the pressurization device is configured such that the gasket retracts in the proximal end direction by a pressure of the liquid medicine that has been increased at a time of the forward rotation of the plunger, without being pulled by the plunger at a time of the reverse rotation of the plunger.

3. The syringe system according to claim 1, wherein the liquid medicine has a viscosity in a range of 50 to 120 mPa·s.

4. A method of using a syringe system, the method comprising:
   providing a syringe system comprising
   a prefilled syringe comprising:
   a barrel,
   a gasket disposed to be slidable inside the barrel, and
   a high-viscosity liquid medicine filled in a liquid chamber formed by the barrel and the gasket; and
   a pressurization device comprising:
   a plunger configured to press the gasket in a distal end direction, wherein the plunger comprises:
   a plunger rod comprising a screw thread at an outer surface of the plunger rod,
   a rotary operation part located at a proximal end portion of the plunger rod,
   a pressing part located at a distal end portion of the plunger rod, and
   a plurality of pressing protrusions that protrude outwardly from the screw thread,
   a grip that is attachable to the barrel of the prefilled syringe and supports the plunger, the grip comprising:
   a barrel attachment part that is attachable to the barrel of the prefilled syringe,
   a female screwing part that is screwed to the screw thread of the plunger, and
   a displacement mechanism part configured to be displaced by the pressing protrusions,
   wherein each of the plurality of pressing protrusions comprises an engaging part extending substantially perpendicular to a circumferential direction of the plunger on a side of the pressing protrusion corresponding to a forward rotation direction of the plunger, and a curved part formed in an arc shape on a side of the pressing protrusion corresponding to a reverse rotation direction of the plunger;
   wherein the pressurization device is configured such that the plunger advances by forward rotation of the plunger, and
   wherein the pressurization device is configured such that the plunger retracts by reverse rotation of the plunger;
   pressing the gasket by the forward rotation of the plunger, thereby applying pressure to the liquid medicine in the barrel to discharge the liquid medicine from the barrel; and
   retracting the plunger without pulling the gasket in a proximal end direction by the reverse rotation of the plunger, whereby the gasket is retracted by a pressure of the liquid medicine in the barrel that has been increased at a time of the forward rotation of the plunger, to stop the discharge of the liquid medicine.

5. The method according to claim 4, wherein the liquid medicine has a viscosity in a range of 50 to 120 mPa·s.

* * * * *